United States Patent [19]
Bandman et al.

[11] Patent Number: 6,080,558
[45] Date of Patent: Jun. 27, 2000

[54] POLYNUCLEOTIDE ENCODING HUMAN GROWTH REGULATOR PROTEIN

[75] Inventors: Olga Bandman, Mountain View; Preeti Lal; Purvi Shah, both of Sunnyvale; Neil C. Corley, Mountain View, all of Calif.

[73] Assignee: Incyte Pharmaceuticals, Inc., Palo Alto, Calif.

[21] Appl. No.: 08/893,852

[22] Filed: Jul. 11, 1997

[51] Int. Cl.$^7$ ..................................................... C12N 15/12
[52] U.S. Cl. .................... 435/69.1; 536/23.5; 435/252.3; 435/254.11; 435/320.1; 435/325
[58] Field of Search ................................ 536/23.5, 24.31; 435/69.1, 325, 252.3, 254.11, 320.1

[56] References Cited

PUBLICATIONS

Liebermann, D.A. et al., "Differentiation Primary Response Genes and Proto–oncogenes as Positive and Negative Regulators of Terminal Hematopoietic Cell Differentiation", *Stem Cells*, 12: 352–369 (1994).

Ron, D. et al., "CHOP, a novel developmentally regulated nuclear protein that dimerizes with transcription factors C/EBP and LAP and Functions as a dominant–negative inhibitor of gene transcription", *Genes Dev.*, 6–439–453 (1992).

Smith, M.L. et al., "Interaction of the p53–Regulated Protein Gadd45 with Proliferating Cell Nuclear Antigen", *Science*, 266:1376–1380 (1994).

Lord, K.A. et al., "Sequence of MyD116 cDNA: a novel myeloid differentiation primary response gene induced by IL6", *Nucleic Acids Res.*, 18: 2823 (1990) (GI 530341).

Lord, K.A. et al., "Dissection of the Immediate Early Response of Myeloid Leukemia Cells to Terminal Differentiation and Growth Inhibitory Stimuli", *Cell Growth Differen.*, 1: 637–645 (1990).

Zhan, Q. et al., "The gadd and MyD Genes Define a Novel Set of Mammalian Genes Encoding Acidic Proteins That Synergistically Suppress Cell Growth", *Molec. Cell. Biol.*, 14: 2361–2371 (1994).

Zhan, Q., (Direct Submission), GenBank Sequence Database (Accession L28147), National Center for Biotechnology Information, National Library of Medicine, Bethesda, Maryland, 20894 (GI 452489; GI 452490).

Lord, K.A. et al., (Direct Submission), GenBank Sequence Database (Accession X51829), National Center for Biotechnology Information, National Library of Medicine, Bethesda, Maryland, 20894 (GI 53040; GI 53041).

*Primary Examiner*—Sally P. Teng
*Attorney, Agent, or Firm*—Collette C. Muenzen, Esq.; Lucy J. Billings, Esq.; Incyte Pharmaceuticals, Inc.

[57] ABSTRACT

The invention provides a new human growth regulator protein (GRREG) and polynucleotides which identify and encode GRREG. The invention also provides expression vectors, host cells, agonists, antibodies and antagonists. The invention also provides methods for treating disorders associated with expression of GRREG.

9 Claims, 10 Drawing Sheets

```
                        9            18            27            36            45            54
5' CAT CCC AGT TGT TGA TCT TAT GCA AGA CGC TGC ACG ACC CCG CGC CCG CTT GTC 63            72            81            90            99           108
   GCC ACG GCA CTT GAG GCA GCC GGA GCC GAT ACT CTG AGT TAC TCG GAG CCC GAC GCC 117           126           135           144           153           162
   TGA GGG TGA GAT GAA CGC GCT GGC CTC CCT AAC CGT CCG GAC CTG TGA TCG CTT 171           180           189           198           207           216
   CTG GCA GAC CGA ACC GGC GCT CCT GCC CCC GGG ACG GTG ACG CGC AGC TCC CAG CCG 225           234           243           252           261           270
   CCC AGA CAC ATG GCC CCA GGC CAA GCA CCC CAT CAG GCT ACC CCG TGG AGG GAT
               M   A   P   G   Q   A   P   H   Q   A   T   P   W   R   D 279           288           297           306           315           324
   GCC CAC CCT TTC TTC CTC CTG TCC CCA GTG ATG AGC CTC CTC AGC CGC GCC TGG
     H   P   F   F   L   L   S   P   V   M   S   L   L   S   R   A   W 333           342           351           360           369           378
   AGC CGC CTG AGG GGC CTG GGA CCT CTA GAG CCC TGG CTG GTG GAA GCA GTA AAA
     R   L   R   G   L   G   P   L   E   P   W   L   V   E   A   V   K
```

FIGURE 1A

```
                387         396         405         414         423         432
GGA GCA GCT CTG GTA GAA GCT GGC CTG GAG GGA GAA GCT AGG ACT CCT CTG GCA
 G   A   A   L   V   E   A   G   L   E   G   E   A   R   T   P   L   A 441         450         459         468         477         486
ATC CCC CAT ACC CCT TGG GGC AGA CGC AGA GAG GAG GCT CCT GAA GAC AGT GGA
 I   P   H   T   P   W   G   R   R   R   E   E   A   P   E   D   S   G 495         504         513         522         531         540
GGC CCT GGA GAG GAC AGA GAA ACA CTG GGG CTG AAA ACC AGC AGT TCC CTT CCT
 G   P   G   E   D   R   E   T   L   G   L   K   T   S   S   S   L   P 549         558         567         576         585         594
GAA GCC TGG GGA CTT TTG GAT GAT GAT GGG TAT GGT GAG CGA GAG GAG CTT CCT
 E   A   W   G   L   L   D   D   D   G   M   Y   G   E   R   E   E   A 603         612         621         630         639         648
ACC AGT GTC CCT AGA GGG CAG GGA AGT CAA TTT GCA GAT GGC CAG CGT GCT CCC
 T   S   V   P   R   G   Q   G   S   Q   F   A   D   G   Q   R   A   P 657         666         675         684         693         702
CTG TCT CCC AGC CTT CTG ATA AGG ACA CTG CAA GGT TCT GAT AAG AAC CCA GGG
 L   S   P   S   L   L   I   R   T   L   Q   G   S   D   K   N   P   G 711         720         729         738         747         756
GAG GAG AAA GCC GAG GAA GAG GAG GTT GCT GAA GAG GAG GGA GGA GTT AAC AAG TTC
 E   E   K   A   E   E   E   E   V   A   E   E   E   G   E   V   N   K   F
```

FIGURE 1B

```
765         774         783         792         801         810
TCT TAT CCA TCA CAC CGG GAG TGT TGT CCA GCC GTG GAG GAG GAC GAT
 S   Y   P   S   H   R   E   C   C   P   A   V   E   E   D   D 819         828         837         846         855         864
GAA GAA GCT GTA AAG AAA GAA GCT CAC AGA ACC TCT ACT TCT GCC TTG TCT CCA
 E   E   A   V   K   K   E   A   H   R   T   S   T   S   A   L   S   P 873         882         891         900         909         918
GGA TCC AAG CCC AGC ACT TGG GTG TCT TGC CCA GGG GAG GAA AAT CAA GCC
 G   S   K   P   S   T   W   V   S   C   P   G   E   E   N   Q   A 927         936         945         954         963         972
ACG GAG GAT AAA ACA GAA AGA AGT AGT AAA GGA GCC AGG AAG ACC TCC GTG TCC
 T   E   D   K   T   E   R   S   S   K   G   A   R   K   T   S   V   S 981         990         999         1008        1017        1026
CCC CGA TCT TCA GGC TCC GAC CCC AGG TGG GAG TAT CGT TCA GGA GAG GCG
 P   R   S   S   G   S   D   P   R   W   E   Y   R   S   G   E   A 1035        1044        1053        1062        1071        1080
TCC GAG AAG GAG AAG GAA AAG GCA CAC GAA GAA ACT GGG AAA GGA GAA GCT GCC
 S   E   K   E   K   E   K   A   H   E   E   T   G   K   G   E   A   A 1089        1098        1107        1116        1125        1134
CCA GGG CCG CAA TCC TCA GCC CCA GCC CAG AGG CCC CAG CTC AAG TCC TGG TGG
 P   G   P   Q   S   S   A   P   A   Q   R   P   Q   L   K   S   W   W
```

FIGURE 1C

```
      1143                1152                1161                1170                1179           1188
TGC CAA CCC AGT GAT GAA GAG GAG AGT GAG GTC AAG GCT TTG GGG GCA GCT GAG
 C   Q   P   S   D   E   E   E   S   E   V   K   A   L   G   A   A   E 1197                1206                1215                1224                1233           1242
AAG GAT GGA GAA GCT GAG TGT CCT GAG TGC ATC CCC CCA CCA AGT GCC TTC CTG
 K   D   G   E   A   E   C   P   E   C   I   P   P   P   S   A   F   L 1251                1260                1269                1278                1287           1296
AAG GCC TGG GTG TAT TGG CCA GGA GAG GAC ACA GAG GAA GAG GAA GAT GAG GAA
 K   A   W   V   Y   W   P   G   E   D   T   E   E   E   E   D   E   E 1305                1314                1323                1332                1341           1350
GAA GAG GAC AGT GAC TCT GGA TCA GAT GAG GAA GAG GGA GGA GAA GCT GAG GCT
 E   E   D   S   D   S   G   S   D   E   E   E   G   G   E   A   E   A 1359                1368                1377                1386                1395           1404
TCC TCT TCC ACT CCT GCT ACA GGT GTC TTC TTG AAG TCC TGG GTC TAT CAG CCA
 S   S   S   T   P   A   T   G   V   F   L   K   S   W   V   Y   Q   P 1413                1422                1431                1440                1449           1458
GGA GAC ACA GAG GAG GAG GAT GAG GAC AGT GAT GAG GAT ACA GGA TCA GCC GAG
 G   D   T   E   E   E   D   E   D   S   D   E   D   T   G   S   A   E 1467                1476                1485                1494                1503           1512
GAT GAA AGA GAA GCT GAG ACT TCT GCT TCC ACA CCC CCT GCA AGT GCT TTC TTG
 D   E   R   E   A   E   T   S   A   S   T   P   P   A   S   A   F   L
```

FIGURE 1D

```
     1521         1530         1539         1548         1557         1566
AAG GCC TGG GTG TAT CGG CCA GGA GAG GAC ACG GAG GAG GAA GAT GAT GAG GAT
 K   A   W   V   Y   R   P   G   E   D   T   E   E   E   D   D   E   D 1575         1584         1593         1602         1611         1620
GTG GAT AGT GAG GAT AAG GAA GAT TCA GAT GCA GCC TTA GAA GGA GAA GCT GAG
 V   D   S   E   D   K   E   D   S   D   A   A   L   E   G   E   A   E 1629         1638         1647         1656         1665         1674
TCA GAC CCA CAT CCC TCC CAC CAG AGT GCC CAC TTC AGG GGC TGG GGA
 S   D   P   H   P   S   H   Q   S   A   H   F   R   G   W   G 1683         1692         1701         1710         1719         1728
TAT CGA CCT GGA AAA GAG ACA GAG GAA GAG GAA GCT GAG GCT GAG GAC TGG GAA
 Y   R   P   G   K   E   T   E   E   E   E   A   E   A   E   D   W   E 1737         1746         1755         1764         1773         1782
GCT GAG CCC TGC CCC TTC CGA GTG GCC ATC TAT GTA CCT GGA GAG AAG CCA CCG
 A   E   P   C   P   F   R   V   A   I   Y   V   P   G   E   K   P   P 1791         1800         1809         1818         1827         1836
CCT TGG GCT CCT CCT AGG CTG CCC CTC CGA CTG CAA AGG CGG CTC AAG CGC
 P   W   A   P   P   R   L   P   L   R   L   Q   R   R   L   K   R 1845         1854         1863         1872         1881         1890
CCT CCC ACC CCT ACT CAT GAT CCG GAC CCT GAG ACT CCC CTA AAG GCC AGA AAG
 P   P   T   P   T   H   D   P   D   P   E   T   P   L   K   A   R   K

CCA GAA
 P   E
```

FIGURE 1E

```
     1899       1908       1917       1926       1935       1944
GTG CGC TTC TCC GAG AAG GTC ACT GTC CAT TTC CTG GCT GTC TGG GCA GGG CCG
 V   R   F   S   E   K   V   T   V   H   F   L   A   V   W   A   G   P 1953       1962       1971       1980       1989       1998
GCC CAG GCC CGC GCC CAG GGC CAG CCC TGG GAG CAG CTT GCT CGG GAT CGC CGC
 A   Q   A   R   A   Q   G   Q   P   W   E   Q   L   A   R   D   R   R 2007       2016       2025       2034       2043       2052
TTC GCA CGC CGC ATC ACC CAG GCC CAG GAG GAG CTG AGC CCC TGC CTC ACC CCT
 F   A   R   R   I   T   Q   A   Q   E   E   L   S   P   C   L   T   P 2061       2070       2079       2088       2097       2106
GCT GCC CGG GCC AGA GCC TGG GCA CGC CTC AGG AAC CCA CCT TTA GCC CCC ATC
 A   A   R   A   R   A   W   A   R   L   R   N   P   P   L   A   P   I 2115       2124       2133       2142       2151       2160
CCT GCC CTC ACC CAG ACC TTG CCT TCC TCC TCT GTC CCT TCG TCC CCA GTC CAG
 P   A   L   T   Q   T   L   P   S   S   S   V   P   S   S   P   V   Q 2169       2178       2187       2196       2205       2214
ACC ACG TTG AGC CAA GCT GTG GCC ACA CCT TCC CGC TCG TCG TCT GCT GCT GCA
 T   T   L   S   Q   A   V   A   T   P   S   R   S   S   S   A   A   A 2223       2232       2241       2250       2259       2268
GCG GCT GCC CTG GAC CTC AGT GGG AGG CGT GGC TGA GAC CAA CTG GTT TGC CTA
 A   A   A   L   D   L   S   G   R   R   G   *   D   Q   L   V   C   L
```

FIGURE 1F

```
            2277          2286          2295          2304          2313          2322
      TAA TTT ATT AAC TAT TTA TTT TTT CTA AGT GTG GGT TTA TAT AAG GAA TAA AGC
            2331          2340
      CTT TTG ATT TGT AAA AAA AAA AAA A 3'
```

FIGURE 1G

```
  1  MAPGQAPHQATPWRDAHPFFLLSPVMSLLSRAWSRLRGLG  508302
  1  MAPSPRPQHVLHWRDAHNFYLLSPLMGLLSRAWSRLRGPE  GI 53041
  1  MAPSPRPQHILLWRDAHSFHLLSPLMGFLSRAWSRLRVPE  GI 452490

41  PLEPWLVEAVKGAALVEAGLEGEARTPLAIPHTPWGRRPE  508302
 41  VPEAWLAKTVTGADQIEAA--ALLTPTPVSGN----LLPH  GI 53041
 41  APEPWPAETVTGADQIEAD--AHPAPPLVPEN----HPPQ  GI 452490

81  EEAEDSGGPGEDRET------LGLKTSSSLPEAWGLLDDDDG  508302
 75  GETEEESGSPEQSAAQRLCL-VEAESSPPETWGLSNVDE--  GI 53041
 75  GEAEESGTPEEGKAAQGPCLDVQANSSPPETLGLSDDD--  GI 452490

117  MYGEREATSVPRGQGSQFADGQRAPLSPSLLIRTLQGSDK  508302
113  -YNAKPGQDDLREKEMERTAGK---ATLQPAGLQGADK  GI 53041
113  ---KQGQDGPREQGPRAHTAGL---PILLSPGLQSADK  GI 452490

157  NPGEEKAEEEGVNKFSYPPSHRECCPAVEEEDDE  508302
147  RLGE-------VVAREEGVAEPAYPTSQLEGGPA-ENEEEDG  GI 53041
144  SLGE-------VVAGEEGVTELAYPTSHWEGCPS-EEEEDG  GI 452490

197  EAVKKEAHRTSTSALSPGSKPSTWVSCPGEEENQATEDKR  508302
180  ETVK---TYQASAASIAPGYKPSTPVPFLGEAAEHQATEEKG  GI 53041
177  ETVKK-AFRASADS--PGHKSSTSVYCPGEAEHQATEEKQ  GI 452490
```

```
463 EAESDPHPSHPDQSAHERGWGYRPGKETEEE--------        508302
428 QTGATPHTS-----PFLKAWVYRPGEDTEDDTEEEDSEN         GI 53041
389 QTFATPHTS-------AFLKTWVCCPGEDTEDD---DCEV        GI 452490

494 -----------------------EAAEDWGEAEPCPFR          508302
463 VAPGDSETADSSQSPCLQPQRCLPGEKTKGRGE-EPPLFQ        GI 53041
419 VVPEDSEAADPDKSPSHEAQGCLPGEQTEGLVEAEHSLFQ        GI 452490

509 VAIYVPGEKPPPPWAPPPRLPLRLQRRLKRPETPTHDPDPE       508302
502 VAFYLPGEKPESPWAAAPKLPLRLQRRLRLFKAPTRDQDPE       GI 53041
459 VAFYLPGEKPAPPWTAPKLPLRLQRRLTLLRTPTQDQDPE        GI 452490

549 TPLKARKVRFSEKVTVHFLAVWAGPAQAAARQGPWEQLARD       508302
542 IPLKARKVHFAEKVTVHFLAVWAGPAQAAARRGPWEQEARD       GI 53041
499 TPLRARKVHFSENVTVHFLAVWAGPAQAAARGPWEQLARD        GI 452490

589 RSRFARRITQAQEELSPCLTPAAARAWARLRNPPLAPIP         508302
582 RSRFARRIAQAEEKLGPYLTPDSRARAWARLRNPSLPQ-         GI 53041
539 RSRFARRIAQAEEKLGPYLTPAFRARAWARLGNPSLP--         GI 452490

629 ALTQTLPSSSVPSSPVQTTPLSQAVATPSR-SSAAAAAAL        508302
620 -----SEPRSSSEATPLTQDVTTPSLPSETPSPSL             GI 53041
576 -----LALEPICDHT                                 GI 452490

668 DLSGRRG                                         508302
651 YLGGRRG                                         GI 53041
586 FFPSQ                                           GI 452490
```

POLYNUCLEOTIDE ENCODING HUMAN GROWTH REGULATOR PROTEIN

FIELD OF THE INVENTION

This invention relates to nucleic acid and amino acid sequences of a new human growth regulator protein and to the use of these sequences in the diagnosis, prevention, and treatment of cancer.

BACKGROUND OF THE INVENTION

Eukaryotic cell numbers are regulated by a balance among proliferation, growth arrest, and apoptosis. Normal cells progress in a regulated fashion through successive stages of cellular growth and differentiation, culminating in growth arrest and apoptosis. Cells exposed to cytotoxic or genotoxic agents deviate from their regulated growth pattern by entering an altered growth stage or by undergoing premature cell death. This cellular response is dependent on specific gene products normally involved in differentiation and apoptosis pathways.

Cell exposed to DNA-damaging agents or differentiation-inducing agents express various genes including the myeloid differentiation primary response genes (MyD) and the growth arrest and DNA damage genes (gadd). Induction of these genes results in inhibition of DNA replication and growth arrest, restricting genetic changes that produce cellular transformation. Members of the MyD family are expressed during the differentiation of myeloid precursor cells into mature granulocytes and macrophages; gadd family members have been found in most cells examined (Liebermann, D. A. and Hoffmann, B. (1994) Stem Cells 12: 352–369).

The gadd genes were first isolated as UV irradiation induced transcripts from chinese hamster ovary cells. These genes are also induced by growth arrest treatments such as starvation and exposure to alkylating agents. The gadd153 and gadd45 genes are expressed and can be specifically induced with alkylating agents in almost all mammalian cells and tissues tested. The gadd153 is the hamster homologue of the human CHOP gene, which codes for a nuclear protein that serves as a dominant-negative inhibitor of the transcription factors C/EBP and LAP. Bacterially expressed CHOP inhibits the DNA-binding activity of C/EBP and LAP by forming heterodimers that cannot bind DNA. CHOP is found to be consistently rearranged in myxoid liposarcomas. GADD45 binds to proliferating cell nuclear antigen, a normal component of cyclin-dependent kinase complexes and a protein involved in DNA replication and repair. GADD45 stimulates DNA excision repair in vitro and inhibits entry of cells into S phase (Ron, D. and Habener, J. F. (1992) Genes Dev. 6: 439–453; Smith, M. L. et al (1994) Science 266: 1376–1380).

The MyD116 gene is the murine homolog of the hamster GADD34 gene. The MyD genes were first isolated from mouse leukemic myeloblasts following induction of terminal differentiation by stimulation with interleukin-6. Members of this gene family control cell growth and regulate cell differentiation by growth inhibition and induction of apoptosis. Activation of MyD116 genes induces myeloblastic leukemia cells to differentiate in vitro and reduces the aggressiveness of their leukemic phenotype in vivo (Lord, K. A. et al (1990) Nucleic Acids Res. 18: 2823; Lord, K. A. et al (1990) Cell Growth Differen. 1: 637–645; and Zhan, Q. et al (1994) Molec. Cell. Biol. 2361–2371).

The discovery of a new human growth regulator protein and the polynucleotides encoding it satisfies a need in the art by providing new compositions which are useful in the diagnosis, prevention, and treatment of cancer.

SUMMARY OF THE INVENTION

The invention features a substantially purified polypeptide, human growth regulator protein (GRREG), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding GRREG under conditions suitable for the expression of the polypeptide; and b) recovering the polypeptide from the host cell culture.

The invention also provides a pharmaceutical composition comprising a substantially purified GRREG having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising at least a fragment of the amino acid sequence of SEQ ID NO:1.

Still further, the invention provides a purified agonist of the polypeptide of SEQ ID NO:1.

The invention also provides a method for treating or preventing cancer comprising administering to a subject in need of such treatment an effective amount of a pharmaceutical composition comprising purified GREGG.

The invention also provides a method for treating or preventing cancer comprising administering to a subject in need of such treatment an effective amount of an agonist which increases the activity of GREGG.

The invention also provides a method for detecting a polynucleotide which encodes GRREG in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding GRREG in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of GRREG. The alignment was produced using MACDNASIS PRO software (Hitachi Software Engineering Co. Ltd. San Bruno, Calif.).

FIGS. 2A, 2B, and 2C show the amino acid sequence alignments among GRREG (SEQ ID NO:1), mouse MyD116 (GI 53041; SEQ ID NO:3) and hamster Gadd34 (GI 452490; SEQ ID NO:4), produced using the multisequence alignment program of DNASTAR software (DNASTAR Inc., Madison, Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

GRREG, as used herein, refers to the amino acid sequences of substantially purified GRREG obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to GRREG, increases or prolongs the duration of the effect of GRREG. Agonists may include proteins, nucleic acids, carbohydrates, or any other molecules which bind to and modulate the effect of GRREG.

An "allele" or "allelic sequence", as used herein, is an alternative form of the gene encoding GRREG. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding GRREG as used herein include those with deletions, insertions, or substitutions of different nucleotides resulting in a polynucleotide that encodes the same or a functionally equivalent GRREG. Included within this definition are polymorphisms which may or may not be readily detectable using a particular oligonucleotide probe of the polynucleotide encoding GRREG, and improper or unexpected hybridization to alleles, with a locus other than the normal chromosomal locus for the polynucleotide sequence encoding GRREG. The encoded protein may also be "altered" and contain deletions, insertions, or substitutions of amino acid residues which produce a silent change and result in a functionally equivalent GRREG. Deliberate amino acid substitutions may be made on the basis of similarity in polarity, charge, solubility, hydrophobicity, hydrophilicity, and/or the amphipathic nature of the residues as long as the biological or immunological activity of GRREG is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of GRREG are preferably about 5 to about 15 amino acids in length and retain the biological activity or the immunological activity of GRREG. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to GRREG, decreases the amount or the duration of the effect of the biological or immunological activity of GRREG. Antagonists may include proteins, nucleic acids, carbohydrates, antibodies or any other molecules which decrease the effect of GRREG.

As used herein, the term "antibody" refers to intact molecules as well as fragments thereof, such as Fab, F(ab')$_2$, and Fv, which are capable of binding the epitopic determinant. Antibodies that bind GRREG polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic GRREG, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding GRREG (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding GRREG in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to GRREG or the encoded GRREG. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear micro-chromosomes which may contain DNA sequences of 10K to 10M in size and contain all of the elements required for stable mitotic chromosome segregation and maintenance (Harrington, J. J. et al. (1997) Nat. Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of GRREG. For example, modulation may cause an increase or a decrease in protein activity, binding characteristics, or any other biological, functional or immunological properties of GRREG.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length GRREG and fragments thereof.

The term "sample", as used herein, is used in its broadest sense. A biological sample suspected of containing nucleic acid encoding GRREG, or fragments thereof, or GRREG itself may comprise a bodily fluid, extract from a cell, chromosome, organelle, or membrane isolated from a cell, a cell, genomic DNA, RNA, or cDNA (in solution or bound to a solid support), a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of GRREG, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human growth regulator protein (hereinafter referred to as "GRREG"), the polynucleotides encoding GRREG, and the use of these compositions for the diagnosis, prevention, or treatment of cancer.

Nucleic acids encoding the GRREG of the present invention were first identified in Incyte Clone 508302 from the peripheral blood mononuclear cell cDNA library (TMLR3DT01) using a computer search for amino acid sequence alignments. A consensus sequence, SEQ ID NO:2, was derived from the following overlapping and/or extended nucleic acid sequences: Incyte Clones 508302 (TMLR3DT01), 779372 (MYOMNOT01), 1727487 (PROSNOT14), and 519908 (MMLR2DT01).

Figure 2B:
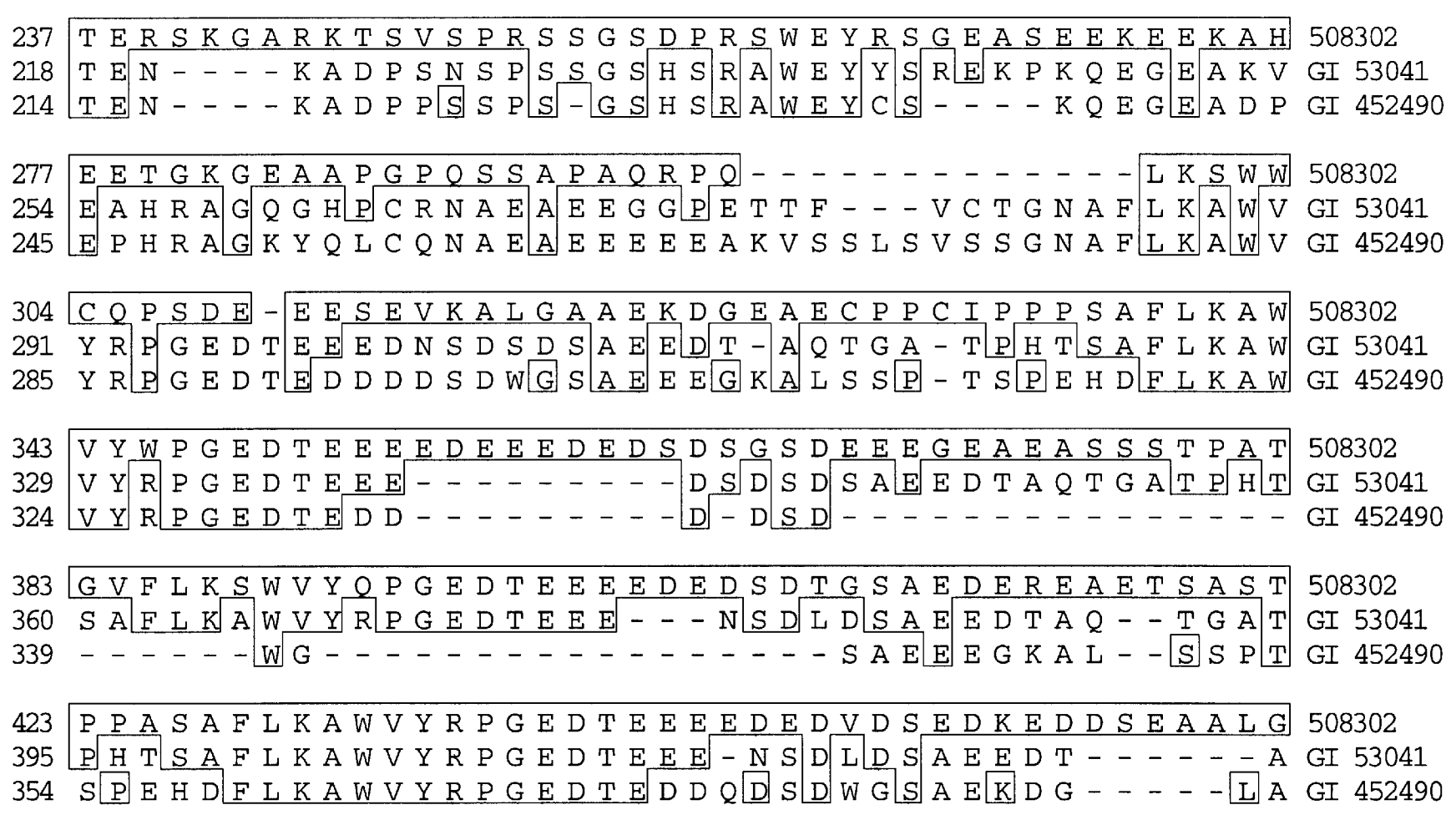

In one embodiment, the invention encompasses a polypeptide comprising the amino acid sequence of SEQ ID NO:1, as shown in FIGS. 1A, 1B, 1C, 1D, 1E, 1F, and 1G. GRREG is 674 amino acids in length and has four similar sequence regions containing PEST sequences, from $A_{337}$–$G_{383}$, $V_{384}$–$S_{426}$, $A_{427}$–$S_{471}$, and $A_{477}$–$P_{518}$. GRREG also contains two potential cAMP-dependent protein kinase phosphorylation sites at residues $S_{247}$ and $T_{597}$, and twelve potential casein kinase II phosphorylation sites at residues $S_{103}$, $S_{182}$, $S_{253}$, $S_{307}$, $T_{350}$, $S_{364}$, $S_{366}$, $T_{397}$, $S_{409}$, $T_{440}$, $S_{471}$, and $T_{490}$. In addition, GRREG contains two potential amidation sites, at residues $W_{75}$ and $S_{670}$, and seven potential protein kinase C phosphorylation sites at $S_{154}$, $S_{182}$, $T_{237}$, $S_{249}$, $T_{279}$, $S_{559}$, and $S_{670}$. As shown in FIGS. 2A, 2B, and 2C, GRREG has chemical and structural homology with mouse MyD116 (SEQ ID NO:3) and hamster Gadd34 (SEQ ID NO:4). In particular, GRREG and mouse MyD116 share 47% identity, and GRREG and hamster Gadd34 share 42% identity.

The invention also encompasses GRREG variants. A preferred GRREG variant is one having at least 80%, and more preferably at least 90%, amino acid sequence identity to the GRREG amino acid sequence (SEQ ID NO:1) and which retains at least one biological, immunological or other functional characteristic or activity of GRREG. A most preferred GRREG variant is one having at least 95% amino acid sequence identity to SEQ ID NO:1.

The invention also encompasses polynucleotides which encode GRREG. Accordingly, any nucleic acid sequence which encodes the amino acid sequence of GRREG can be used to produce recombinant molecules which express GRREG. In a particular embodiment, the invention encompasses the polynucleotide comprising the nucleic acid sequence of SEQ ID NO:2 as shown in FIGS. 1A, 1B, 1C, 1D, 1E, 1F, and 1G.

It will be appreciated by those skilled in the art that as a result of the degeneracy of the genetic code, a multitude of nucleotide sequences encoding GRREG, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring GRREG, and all such variations are to be considered as being specifically disclosed.

Although nucleotide sequences which encode GRREG and its variants are preferably capable of hybridizing to the nucleotide sequence of the naturally occurring GRREG under appropriately selected conditions of stringency, it may be advantageous to produce nucleotide sequences encoding GRREG or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GRREG and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode GRREG and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding GRREG or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.), and the ABI CATALYST and 373 and 377 DNA sequencers (Perkin Elmer).

The nucleic acid sequences encoding GRREG may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic.

1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode GRREG may be used in recombinant DNA molecules to direct expression of GRREG, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express GRREG.

As will be understood by those of skill in the art, it may be advantageous to produce GRREG-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter GRREG encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding GRREG may be ligated to a heterologous sequence to encode a fusion protein. For example, to screen peptide libraries for inhibitors of GRREG activity, it may be useful to encode a chimeric GRREG protein that can be recognized by a commercially available antibody. A fusion protein may also be engineered to contain a cleavage site located between the GRREG encoding sequence and the heterologous protein sequence, so that GRREG may be cleaved and purified away from the heterologous moiety.

In another embodiment, sequences encoding GRREG may be synthesized, in whole or in part, using chemical methods well known in the art (see Caruthers, M. H. et al. (1980) Nucl. Acids Res. Symp. Ser. 215–223; Horn, T. et al. (1980) Nucl. Acids Res. Symp. Ser. 225–232). Alternatively, the protein itself may be produced using chemical methods to synthesize the amino acid sequence of GRREG, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of GRREG, or any part thereof, may be altered during direct synthesis and/or combined using chemical methods with sequences from other proteins, or any part thereof, to produce a variant polypeptide.

In order to express a biologically active GRREG, the nucleotide sequences encoding GRREG or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding GRREG and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding GRREG. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding GRREG, vectors based on SV40 or EBV may be used with an appropriate selectable marker.

In bacterial systems, a number of expression vectors may be selected depending upon the use intended for GRREG. For example, when large quantities of GRREG are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding GRREG may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding GRREG may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express GRREG. For example, in one such system, *Autographa californica* nuclear polyhedrosis virus (AcNPV) is used as a vector to express foreign genes in *Spodoptera frugiperda* cells or in Trichoplusia larvae. The sequences encoding GRREG may be cloned into a non-essential region of the virus, such as the polyhedrin gene, and placed under control of the polyhedrin promoter. Successful insertion of GRREG will render the polyhedrin gene inactive and produce recombinant virus lacking coat protein. The recombinant viruses may then be used to infect, for example, *S. frugiperda* cells or Trichoplusia larvae in which GRREG may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding GRREG may be ligated into an adenovirus transcription/translation complex consisting of the late promoter and tripartite leader sequence. Insertion in a non-essential E1 or E3 region of the viral genome may be used to obtain a viable virus which is capable of expressing GRREG in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACS) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding GRREG. Such signals include the ATG initiation codon and adjacent sequences. In cases where sequences encoding GRREG, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express GRREG may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding GRREG is inserted within a marker gene sequence, transformed cells containing sequences encoding GRREG can be identified by the absence of marker gene function. Alternatively, a marker gene can be placed in tandem with a sequence encoding GRREG under the control of a single promoter. Expression of the marker gene in response to induction or selection usually indicates expression of the tandem gene as well.

Alternatively, host cells which contain the nucleic acid sequence encoding GRREG and express GRREG may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding GRREG can be detected by DNA-DNA or DNA-RNA hybridization or amplification using probes or fragments or fragments of polynucleotides encoding GRREG. Nucleic acid amplification based assays involve the use of oligonucleotides or oligomers based on the sequences encoding GRREG to detect transformants containing DNA or RNA encoding GRREG.

A variety of protocols for detecting and measuring the expression of GRREG, using is either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on GRREG is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GRREG include oligolabeling, nick translation, end-labeling or PCR amplification using a labeled nucleotide. Alternatively, the sequences encoding GRREG, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp. (Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding GRREG may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode GRREG may be designed to contain signal sequences which direct secretion of GRREG through a prokaryotic or eukaryotic cell membrane. Other constructions may be used to join sequences encoding GRREG to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and GRREG may be used to facilitate purification. One such expression vector provides for expression of a fusion protein containing GRREG and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying GRREG from the fusion protein. A discussion of vectors which contain fusion proteins is provided in Kroll, D. J. et al. (1993; DNA Cell Biol. 12:441–453).

In addition to recombinant production, fragments of GRREG may be produced by direct peptide synthesis using solid-phase techniques (Merrifield, J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of GRREG may be chemically synthesized separately and combined using chemical methods to produce the full length molecule.

THERAPEUTICS

Proteins regulating cell differentiation can act on a specific gene transcript or regulate the expression of a variety of genes by modulating the expression of key proteins within a cellular pathway. Proteins that determine cellular differentiation play a key role in maintaining normal cell homeostasis and function. Chemical and structural homology exists among GRREG, mouse MyD116 (GI 53041; SEQ ID NO:3) and hamster Gadd34 (GI 452490; SEQ ID NO:4). Therefore, GRREG appears to play a role in regulating cell growth, differentiation, and apoptosis.

Therefore, in one embodiment, GRREG or a fragment or derivative may be administered to a subject to treat or prevent cancer. These cancers include, but are not limited to, adenocarcinoma, leukemia, lymphoma, melanoma, myeloma, sarcoma, and teratocarcinoma and particularly cancers of the adrenal gland, bladder, bone, brain, breast, cervix, gall bladder, gastrointestinal tract, heart, kidney, liver, lung, ovaries, pancreas, paragangliomas, parathyroid, pituitary gland, prostate, salivary gland, spleen, stomach, thymus, thyroid, testes, and uterus.

In another embodiment, a vector capable of expressing GRREG, or a fragment or a derivative thereof, may also be administered to a subject to treat cancers including, but not limited to, those described above.

In one embodiment, an agonist of GRREG may be administered to a subject to prevent or treat cancers including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GRREG may be produced using methods which are generally known in the art. In particular, purified GRREG may be used to produce antibodies or to screen libraries of pharmaceutical agents to identify those which specifically bind GRREG.

Antibodies to GRREG may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with GRREG or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GRREG have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of GRREG amino acids may be fused with those of another protein such as keyhole limpet hemocyanin and antibody produced against the chimeric molecule.

Monoclonal antibodies to GRREG may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce GRREG-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for GRREG may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GRREG and its specific antibody. A two-site, monoclonal-based immunoassay utilizing monoclonal antibodies reactive to two non-interfering GRREG epitopes is preferred, but a competitive binding assay may also be employed (Maddox, supra).

In another embodiment of the invention, the polynucleotides encoding GRREG, or any fragment or complement thereof, may be used for therapeutic purposes. In one aspect, the complement of the polynucleotide encoding GRREG may be used in situations in which it would be desirable to block the transcription of the mRNA. In particular, cells may be transformed with sequences complementary to polynucleotides encoding GRREG. Thus, complementary molecules or fragments may be used to modulate GRREG activity, or to achieve regulation of gene function. Such technology is now well known in the art, and sense or antisense oligonucleotides or larger fragments, can be designed from various locations along the coding or control regions of sequences encoding GRREG.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding GRREG. These techniques are described both in Sambrook et al. (supra) and in Ausubel et al. (supra).

Genes encoding GRREG can be turned off by transforming a cell or tissue with expression vectors which express high levels of a polynucleotide or fragment thereof which encodes GRREG. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding GRREG (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding GRREG.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GRREG. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of GRREG, antibodies to GRREG, mimetics, agonists, antagonists, or inhibitors of GRREG. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of GRREG, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example GRREG or fragments thereof, antibodies of GRREG, agonists, antagonists or inhibitors of GRREG, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GRREG may be used for the diagnosis of conditions or diseases characterized by expression of GRREG, or in assays to monitor patients being treated with GRREG, agonists, antagonists or inhibitors. The antibodies useful for diagnostic purposes may be prepared in the same manner as those described above for therapeutics. Diagnostic assays for GRREG include methods which utilize the antibody and a label to detect GRREG in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring GRREG are known in the art and provide a basis for diagnosing altered or abnormal levels of GRREG expression. Normal or standard values for GRREG expression are established by combining body fluids or cell extracts taken from normal mammalian subjects, preferably human, with antibody to GRREG under conditions suitable for complex formation. The amount of standard complex formation may be quantified by various methods, but preferably by photometric, means. Quantities of GRREG expressed in subject samples from biopsied tissues are compared with the standard values. Deviation between standard and subject values establishes the parameters for diagnosing disease.

In another embodiment of the invention, the polynucleotides encoding GRREG may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GRREG may be correlated with disease. The diagnostic assay may be used to distinguish between absence, presence, and excess expression of GRREG, and to monitor regulation of GRREG levels during therapeutic intervention.

In one aspect, hybridization with PCR probes which are capable of detecting polynucleotide sequences, including genomic sequences, encoding GRREG or closely related molecules, may be used to identify nucleic acid sequences which encode GRREG. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding GRREG, alleles, or related sequences.

Probes may also be used for the detection of related sequences, and should preferably contain at least 50% of the nucleotides from any of the GRREG encoding sequences. The hybridization probes of the subject invention may be DNA or RNA and derived from the nucleotide sequence of SEQ ID NO:2 or from genomic sequence including promoter, enhancer elements, and introns of the naturally occurring GRREG.

Means for producing specific hybridization probes for DNAs encoding GRREG include the cloning of nucleic acid sequences encoding GRREG or GRREG derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding GRREG may be used for the diagnosis of conditions or disorders which are associated with expression of GRREG. Examples of such conditions or disorders include adenocarcinoma, leukemia, lymphoma, melanoma, myeloma, sarcoma, and teratocarcinoma and particularly cancers of the adrenal gland, bladder, bone, brain, breast, cervix, gall bladder, gastrointestinal tract, heart, kidney, liver, lung, ovaries, pancreas, paragangliomas, parathyroid, pituitary gland, prostate, salivary gland, spleen, stomach, thymus, thyroid, testes, and uterus. The polynucleotide sequences encoding GRREG may be used in Southern or northern analysis, dot blot, or other membrane-based technologies; in PCR technologies; or in dipstick, pin, ELISA assays or microarrays utilizing fluids or tissues from patient biopsies to detect altered GRREG expression. Such qualitative or quantitative methods are well known in the art.

In a particular aspect, the nucleotide sequences encoding GRREG may be useful in assays that detect activation or induction of various cancers, particularly those mentioned above. The nucleotide sequences encoding GRREG may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding GRREG in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of GRREG, a normal or standard profile for expression is established. This may be accomplished by combining body fluids or cell extracts taken from normal subjects, either animal or human, with a sequence, or a fragment thereof, which encodes GRREG, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GRREG may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of GRREG include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode GRREG may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding GRREG on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, GRREG, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between GRREG and the agent being tested, may be measured.

Another technique for drug screening which may be used provides for high throughput screening of compounds having suitable binding affinity to the protein of interest as described in published PCT application WO84/03564. In this method, as applied to GRREG large numbers of different small test compounds are synthesized on a solid substrate, such as plastic pins or some other surface. The test compounds are reacted with GRREG, or fragments thereof, and washed. Bound GRREG is then detected by methods well known in the art. Purified GRREG can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GRREG specifically compete with a test compound for binding GRREG. In this manner, the antibodies can be used to detect the presence of any peptide which shares one or more antigenic determinants with GRREG.

In additional embodiments, the nucleotide sequences which encode GRREG may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I TMLR3DT01 cDNA Library Construction

The TMLR3DT01 cDNA library was prepared from peripheral blood T-lymphocytes obtained from two 24 year old, Caucasian males. This library represents a mixture of allogeneically stimulated human T cell populations obtained from Ficoll/Hypaque purified buffy coats. The cells from the two different donors (not typed for HLA alleles) were incubated at a density of $1\times10^6$/ml, cultured for 72 hours in DME containing 10% human serum, washed in PBS, scraped and lysed immediately in buffer containing guanidinium isothiocyanate. The lysate was extracted twice with a mixture of phenol and chloroform, pH 8.0 and centrifuged over a CsCl cushion using Beckman SW28 rotor in a L8-70M ultracentrifuge (Beckman Instruments). The RNA was precipitated using 0.3 M sodium acetate and 2.5 volumes of ethanol, resuspended in water and DNase treated for 15 min at 37° C. The poly $A^+$ RNA was isolated using the OLIGOTEX kit (QIAGEN Inc., Chatsworth, Calif.). It must be noted that B lymphocytes were not removed, and some contaminating macrophages may also have been present.

Stratagene (La Jolla, Calif.) used the total RNA to construct a custom cDNA library. First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated on SEPHACRYL S400 to obtain sequences which exceeded 1000 bp in size. The size-selected cDNAs were inserted into the LAMBDAZAP vector system (Stratagene); and the vector which contains the PBLUESCRIPT phagemid (Stratagene) was transformed into cells of *E. coli*, strain XL1-BLUEMRF (Stratagene).

The phagemid forms of individual cDNA clones were obtained by the in vivo excision process. Enzymes from both PBLUESCRIPT and a co-transformed f1 helper phage nicked the DNA, initiated new DNA synthesis, and created the smaller, single-stranded, circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones

Plasmid DNA was released from the cells and purified using the MINIPREP kit (Catalogue #77468; Advanced Genetic Technologies Corporation, Gaithersburg, Md.). This kit consists of a 96 well block with reagents for 960 purifications. The recommended protocol was employed except for the following changes: 1) the 96 wells were each filled with only 1 ml of sterile Terrific Broth (Catalog #22711, Gibco/BRL, Gaithersburg, Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS DNA purification system (Catalogue #A7100, Promega, Madison, Wis.) or QIAwell-8 plasmid, QIAWELL PLUS DNA and QIAWELL ULTRA DNA purification systems (QIAGEN, Chatsworth, Calif.).

The cDNAs were sequenced by the method of Sanger F and AR Coulson (1975; J Mol Biol 94:441f), using a MICROLAB 2200 (Hamilton, Reno, Nev.) in combination with four Peltier thermal cyclers (PTC200 from MJ Research, Watertown, Mass.) and Applied Biosystems 377 or 373 DNA sequencing systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S F (1993) J Mol Evol 36:290–300; Altschul, S F et al (1990) J Mol Biol 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the minimum length of the sequences in the Sequence Listing is 49 nucleotides, and the upper limit of uncalled bases where N is recorded rather than A, C, G, or T is 12%.

The BLAST approach, as detailed in Karlin and Altschul (1993; Proc Nat Acad Sci 90:5873–7) and incorporated herein by reference searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequence were searched against the GenBank databases for primate (pri), rodent (rod), and mammalian sequences (mam). Deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J.Mol.Evol.* 36:290–300; Altschul, S. F. et al. (1990) *J.Mol.Evol.* 215:403–410) are used to search for identical or related molecules in nucleotide databases such as GenBank or the LIFESEQ (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding GRREG occurs. Abundance and percent abundance are also reported. Abundance directly reflects the number of times a particular transcript is represented in a cDNA library, and percent abundance is abundance divided by the total number of sequences examined in the cDNA library.

V Extension of GRREG Encoding Polynucleotides

The nucleic acid sequence of the Incyte Clone 508302 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| Step | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 µCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing 10$^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR film (Kodak, Rochester, N.Y.) is exposed to the blots, or the blots are exposed in a Phosphoimager cassette (Molecular Dynamics, Sunnyvale, Calif.), hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the microarray.

VIII Complementary Polynucleotides

Sequence complementary to the GRREG-encoding sequence, or any part thereof, is used to decrease or inhibit expression of naturally occurring GRREG. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of GRREG, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GRREG-encoding transcript.

IX Expression of GRREG

Expression of GRREG is accomplished by subcloning the cDNAs into appropriate vectors and transforming the vectors into host cells. In this case, the cloning vector is also used to express GRREG in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of GRREG into the bacterial growth media which can be used directly in the following assay for activity.

X Demonstration of GRREG Activity

GRREG activity may be demonstrated in a transient transfection assay in which an expression vector encoding GRREG is used to express GRREG in a tumor cell line. The transfected cells expressing GRREG are subsequently assayed for indicators of differentiation and growth inhibition including a decrease in the rate of cell division and the appearance of differentiation-associated markers such as the $C_3$ and Fc receptors.

GRREG may be transformed into a mammalian tumor cell line such as RKO, H1299, HeLa, or M1 (ATCC) with an eukaryotic expression vector encoding GRREG. Eukaryotic expression vectors are commercially available, and the techniques to introduce them into cells are well known to those skilled in the art. The cells are incubated for two weeks after transformation under conditions appropriate for the cell line to allow expression of GRREG.

Changes in the cell growth rates can be assessed be fixing, staining, and counting cells at regular intervals after transfection, and C3 and Fc receptor appearance can be determined by erythrocyte rosette formation. Sheep erythrocytes are coated with rabbit-anti sheep antibody (1:1000 dilution), washed, then incubated with a 1:10 dilution of mouse serum as a source of complement. $10^8$ erythrocytes are mixed with $10^6$ cells in a 1 ml final volume, centrifuged for 3 mins at 500×g, and incubated at 37° C. for 30 mins. The pellet is then gently dispersed and the percentage of cells with 5 or more attached erythrocytes is counted in a hemocytometer.

XI Production of GRREG Specific Antibodies

GRREG that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring GRREG Using Specific Antibodies

Naturally occurring or recombinant GRREG is substantially purified by immunoaffinity chromatography using antibodies specific for GRREG. An immunoaffinity column is constructed by covalently coupling GRREG antibody to an activated chromatographic resin, such as CNBr-activated SEPHAROSE (Pharmacia & Upjohn). After the coupling, the resin is blocked and washed according to the manufacturer's instructions.

Media containing GRREG is passed over the immunoaffinity column, and the column is washed under conditions that allow the preferential absorbance of GRREG (e.g., high ionic strength buffers in the presence of detergent). The column is eluted under conditions that disrupt antibody/GRREG binding (eg, a buffer of pH 2–3 or a high concentration of a chaotrope, such as urea or thiocyanate ion), and GRREG is collected.

XIII Identification of Molecules Which Interact with GRREG

GRREG or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled GRREG, washed and any wells with labeled GRREG complex are assayed. Data obtained using different concentrations of GRREG are used to calculate values for the number, affinity, and association of GRREG with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEQ ID NO:1.

2. A composition comprising the polynucleotide of claim 1 and a detectable label.

3. An isolated and purified polynucleotide which is complementary to the polynucleotide of claim 1.

4. An expression vector containing the polynucleotide of claim 1.

5. An isolated host cell transformed or transfected with the expression vector of claim 4.

6. A method for producing a polypeptide comprising the amino acid sequence of SEQ ID NO:1, the method comprising the steps of:
   a) culturing the host cell of claim 5 under conditions suitable for the expression of the polypeptide; and
   b) recovering the polypeptide from the host cell culture.

7. An isolated and purified polynucleotide comprising SEQ ID NO:2.

8. A composition comprising the polynucleotide of claim 7 and a detectable label.

9. An isolated and purified polynucleotide which is complementary to the polynucleotide of claim 7.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 674 amino acids
      (B) TYPE: amino acid
      (C) STRANDEDNESS: single
      (D) TOPOLOGY: linear (vii) IMMEDIATE SOURCE:
    (A) LIBRARY: TMLR3DT01
    (B) CLONE: 508302

(xi) SEQUENCE DESCRIPTION: SEQ ID NO:1:

```
Met Ala Pro Gly Gln Ala Pro His Gln Ala Thr Pro Trp Arg Asp Ala
 1               5                  10                  15

His Pro Phe Phe Leu Leu Ser Pro Val Met Ser Leu Leu Ser Arg Ala
            20                  25                  30

Trp Ser Arg Leu Arg Gly Leu Gly Pro Leu Glu Pro Trp Leu Val Glu
        35                  40                  45

Ala Val Lys Gly Ala Ala Leu Val Glu Ala Gly Leu Glu Gly Glu Ala
    50                  55                  60

Arg Thr Pro Leu Ala Ile Pro His Thr Pro Trp Gly Arg Arg Pro Glu
65                  70                  75                  80

Glu Glu Ala Glu Asp Ser Gly Pro Gly Asp Arg Glu Thr Leu
                85                  90                  95

Gly Leu Lys Thr Ser Ser Ser Leu Pro Glu Ala Trp Gly Leu Leu Asp
            100                 105                 110

Asp Asp Asp Gly Met Tyr Gly Glu Arg Glu Ala Thr Ser Val Pro Arg
            115                 120                 125

Gly Gln Gly Ser Gln Phe Ala Asp Gly Gln Arg Ala Pro Leu Ser Pro
            130                 135                 140

Ser Leu Leu Ile Arg Thr Leu Gln Gly Ser Asp Lys Asn Pro Gly Glu
145                 150                 155                 160

Glu Lys Ala Glu Glu Glu Gly Val Ala Glu Glu Gly Val Asn Lys
                165                 170                 175

Phe Ser Tyr Pro Pro Ser His Arg Glu Cys Cys Pro Ala Val Glu Glu
            180                 185                 190

Glu Asp Glu Glu Ala Val Lys Lys Glu Ala His Arg Thr Ser Thr
            195                 200                 205

Ser Ala Leu Ser Pro Gly Ser Lys Pro Ser Thr Trp Val Ser Cys Pro
    210                 215                 220

Gly Glu Glu Asn Gln Ala Thr Glu Asp Lys Arg Thr Glu Arg Ser
225                 230                 235                 240

Lys Gly Ala Arg Lys Thr Ser Val Ser Pro Arg Ser Ser Gly Ser Asp
            245                 250                 255

Pro Arg Ser Trp Glu Tyr Arg Ser Gly Glu Ala Ser Glu Glu Lys Glu
            260                 265                 270

Glu Lys Ala His Glu Glu Thr Gly Lys Gly Glu Ala Ala Pro Gly Pro
    275                 280                 285

Gln Ser Ser Ala Pro Ala Gln Arg Pro Gln Leu Lys Ser Trp Trp Cys
    290                 295                 300

Gln Pro Ser Asp Glu Glu Glu Ser Glu Val Lys Ala Leu Gly Ala Ala
305                 310                 315                 320

Glu Lys Asp Gly Glu Ala Glu Cys Pro Pro Cys Ile Pro Pro Ser
            325                 330                 335

Ala Phe Leu Lys Ala Trp Val Tyr Trp Pro Gly Glu Asp Thr Glu Glu
            340                 345                 350

Glu Glu Asp Glu Glu Glu Asp Glu Asp Ser Asp Ser Gly Ser Asp Glu
            355                 360                 365

Glu Glu Gly Glu Ala Glu Ala Ser Ser Ser Thr Pro Ala Thr Gly Val
    370                 375                 380
```

```
Phe Leu Lys Ser Trp Val Tyr Gln Pro Gly Glu Asp Thr Glu Glu Glu
385                 390                 395                 400

Glu Asp Glu Asp Ser Asp Thr Gly Ser Ala Glu Asp Glu Arg Glu Ala
            405                 410                 415

Glu Thr Ser Ala Ser Thr Pro Pro Ala Ser Ala Phe Leu Lys Ala Trp
                420                 425                 430

Val Tyr Arg Pro Gly Glu Asp Thr Glu Glu Glu Asp Glu Asp Val
        435                 440                 445

Asp Ser Glu Asp Lys Glu Asp Asp Ser Glu Ala Ala Leu Gly Glu Ala
        450                 455                 460

Glu Ser Asp Pro His Pro Ser His Pro Asp Gln Ser Ala His Phe Arg
465                 470                 475                 480

Gly Trp Gly Tyr Arg Pro Gly Lys Glu Thr Glu Glu Glu Ala Ala
                485                 490                 495

Glu Asp Trp Gly Glu Ala Glu Pro Cys Pro Phe Arg Val Ala Ile Tyr
                500                 505                 510

Val Pro Gly Glu Lys Pro Pro Pro Trp Ala Pro Pro Arg Leu Pro
            515                 520                 525

Leu Arg Leu Gln Arg Arg Leu Lys Arg Pro Glu Thr Pro Thr His Asp
530                 535                 540

Pro Asp Pro Glu Thr Pro Leu Lys Ala Arg Lys Val Arg Phe Ser Glu
545                 550                 555                 560

Lys Val Thr Val His Phe Leu Ala Val Trp Ala Gly Pro Ala Gln Ala
                565                 570                 575

Ala Arg Gln Gly Pro Trp Glu Gln Leu Ala Arg Asp Arg Ser Arg Phe
                580                 585                 590

Ala Arg Arg Ile Thr Gln Ala Gln Glu Glu Leu Ser Pro Cys Leu Thr
                595                 600                 605

Pro Ala Ala Arg Ala Arg Ala Trp Ala Arg Leu Arg Asn Pro Pro Leu
            610                 615                 620

Ala Pro Ile Pro Ala Leu Thr Gln Thr Leu Pro Ser Ser Ser Val Pro
625                 630                 635                 640

Ser Ser Pro Val Gln Thr Thr Pro Leu Ser Gln Ala Val Ala Thr Pro
                645                 650                 655

Ser Arg Ser Ser Ala Ala Ala Ala Ala Leu Asp Leu Ser Gly Arg
                660                 665                 670

Arg Gly (2) INFORMATION FOR SEQ ID NO:2:

(i) SEQUENCE CHARACTERISTICS:
        (A) LENGTH: 2344 base pairs
        (B) TYPE: nucleic acid
        (C) STRANDEDNESS: single
        (D) TOPOLOGY: linear (vii) IMMEDIATE SOURCE:
        (A) LIBRARY: TMLR3DT01
        (B) CLONE: 508302

(xi) SEQUENCE DESCRIPTION: SEQ ID NO:2:

CATCCCAGTT GTTGATCTTA TGCAAGACGC TGCACGACCC CGCGCCCGCT TGTCGCCACG      60

GCACTTGAGG CAGCCGGAGA TACTCTGAGT TACTCGGAGC CCGACGCCTG AGGGTGAGAT     120

GAACGCGCTG GCCTCCCTAA CCGTCCGGAC CTGTGATCGC TTCTGGCAGA CCGAACCGGC     180

GCTCCTGCCC CCGGGGTGAC GCGCAGCTCC CAGCCGCCCA GACACATGGC CCCAGGCCAA     240
```

```
GCACCCCATC AGGCTACCCC GTGGAGGGAT GCCCACCCTT TCTTCCTCCT GTCCCCAGTG      300

ATGAGCCTCC TCAGCCGCGC CTGGAGCCGC CTGAGGGGCC TGGGACCTCT AGAGCCCTGG      360

CTGGTGGAAG CAGTAAAAGG AGCAGCTCTG GTAGAAGCTG GCCTGGAGGG AGAAGCTAGG      420

ACTCCTCTGG CAATCCCCCA TACCCCTTGG GGCAGACGCC CTGAAGAGGA GGCTGAAGAC      480

AGTGGAGGCC CTGGAGAGGA CAGAGAAACA CTGGGGCTGA AAACCAGCAG TTCCCTTCCT      540

GAAGCCTGGG GACTTTTGGA TGATGATGAT GGCATGTATG GTGAGCGAGA GGCAACCAGT      600

GTCCCTAGAG GGCAGGGAAG TCAATTTGCA GATGGCCAGC GTGCTCCCCT GTCTCCCAGC      660

CTTCTGATAA GGACACTGCA AGGTTCTGAT AAGAACCCAG GGGAGGAGAA AGCCGAGGAA      720

GAGGGAGTTG CTGAAGAGGA GGGAGTTAAC AAGTTCTCTT ATCCACCATC ACACCGGGAG      780

TGTTGTCCAG CCGTGGAGGA GGAGGACGAT GAAGAAGCTG TAAAGAAAGA AGCTCACAGA      840

ACCTCTACTT CTGCCTTGTC TCCAGGATCC AAGCCCAGCA CTTGGGTGTC TTGCCCAGGG      900

GAGGAAGAGA ATCAAGCCAC GGAGGATAAA AGAACAGAAA GAAGTAAAGG AGCCAGGAAG      960

ACCTCCGTGT CCCCCCGATC TTCAGGCTCC GACCCCAGGT CCTGGGAGTA TCGTTCAGGA     1020

GAGGCGTCCG AGGAGAAGGA GGAAAAGGCA CACGAAGAAA CTGGGAAAGG AGAAGCTGCC     1080

CCAGGGCCGC AATCCTCAGC CCCAGCCCAG AGGCCCCAGC TCAAGTCCTG GTGGTGCCAA     1140

CCCAGTGATG AAGAGGAGAG TGAGGTCAAG GCTTTGGGGG CAGCTGAGAA GGATGGAGAA     1200

GCTGAGTGTC CTCCCTGCAT CCCCCCACCA AGTGCCTTCC TGAAGGCCTG GGTGTATTGG     1260

CCAGGAGAGG ACACAGAGGA AGAGGAAGAT GAGGAAGAAG ATGAGGACAG TGACTCTGGA     1320

TCAGATGAGG AAGAGGGAGA AGCTGAGGCT TCCTCTTCCA CTCCTGCTAC AGGTGTCTTC     1380

TTGAAGTCCT GGGTCTATCA GCCAGGAGAG GACACAGAGG AGGAGGAAGA TGAGGACAGT     1440

GATACAGGAT CAGCCGAGGA TGAAAGAGAA GCTGAGACTT CTGCTTCCAC ACCCCCTGCA     1500

AGTGCTTTCT TGAAGGCCTG GGTGTATCGG CCAGGAGAGG ACACGGAGGA GGAGGAAGAT     1560

GAGGATGTGG ATAGTGAGGA TAAGGAAGAT GATTCAGAAG CAGCCTTAGG AGAAGCTGAG     1620

TCAGACCCAC ATCCCTCCCA CCCGGACCAG AGTGCCCACT TCAGGGGCTG GGATATCGA     1680

CCTGGAAAAG AGACAGAGGA AGAGGAAGCT GCTGAGGACT GGGGAGAAGC TGAGCCCTGC     1740

CCCTTCCGAG TGGCCATCTA TGTACCTGGA GAGAAGCCAC CGCCTCCCTG GGCTCCTCCT     1800

AGGCTGCCCC TCCGACTGCA AAGGCGGCTC AAGCGCCCAG AAACCCCTAC TCATGATCCG     1860

GACCCTGAGA CTCCCCTAAA GGCCAGAAAG GTGCGCTTCT CCGAGAAGGT CACTGTCCAT     1920

TTCCTGGCTG TCTGGGCAGG GCCGGCCCAG GCCGCCCGCC AGGGCCCCTG GGAGCAGCTT     1980

GCTCGGGATC GCAGCCGCTT CGCACGCCGC ATCACCCAGG CCCAGGAGGA GCTGAGCCCC     2040

TGCCTCACCC CTGCTGCCCG GGCCAGAGCC TGGGCACGCC TCAGGAACCC ACCTTTAGCC     2100

CCCATCCCTG CCCTCACCCA GACCTTGCCT TCCTCCTCTG TCCCTTCGTC CCCAGTCCAG     2160

ACCACGCCCT TGAGCCAAGC TGTGGCCACA CCTTCCCGCT CGTCTGCTGC TGCAGCGGCT     2220

GCCCTGGACC TCAGTGGGAG GCGTGGCTGA GACCAACTGG TTTGCCTATA ATTTATTAAC     2280

TATTTATTTT TTCTAAGTGT GGGTTTATAT AAGGAATAAA GCCTTTTGAT TTGTAAAAAA     2340

AAAA                                                                2344
```

(2) INFORMATION FOR SEQ ID NO:3:

(i) SEQUENCE CHARACTERISTICS:
        (A) LENGTH: 657 amino acids
        (B) TYPE: amino acid
        (C) STRANDEDNESS: single -continued

```
        (D) TOPOLOGY: linear (vii) IMMEDIATE SOURCE:
         (A) LIBRARY: GenBank
         (B) CLONE: 53041

(xi) SEQUENCE DESCRIPTION: SEQ ID NO:3:

Met Ala Pro Ser Pro Arg Pro Gln His Val Leu His Trp Arg Asp Ala
  1               5                  10                  15

His Asn Phe Tyr Leu Leu Ser Pro Leu Met Gly Leu Leu Ser Arg Ala
             20                  25                  30

Trp Ser Arg Leu Arg Gly Pro Glu Val Pro Glu Ala Trp Leu Ala Lys
         35                  40                  45

Thr Val Thr Gly Ala Asp Gln Ile Glu Ala Ala Leu Leu Thr Pro
 50                  55                  60

Thr Pro Val Ser Gly Asn Leu Leu Pro His Gly Glu Thr Glu Glu Ser
 65                  70                  75                  80

Gly Ser Pro Glu Gln Ser Gln Ala Ala Gln Arg Leu Cys Leu Val Glu
                 85                  90                  95

Ala Glu Ser Ser Pro Pro Glu Thr Trp Gly Leu Ser Asn Val Asp Glu
                100                 105                 110

Tyr Asn Ala Lys Pro Gly Gln Asp Asp Leu Arg Glu Lys Glu Met Glu
            115                 120                 125

Arg Thr Ala Gly Lys Ala Thr Leu Gln Pro Ala Gly Leu Gln Gly Ala
130                 135                 140

Asp Lys Arg Leu Gly Glu Val Val Ala Arg Glu Gly Val Ala Glu
145                 150                 155                 160

Pro Ala Tyr Pro Thr Ser Gln Leu Glu Gly Gly Pro Ala Glu Asn Glu
                165                 170                 175

Glu Asp Gly Glu Thr Val Lys Thr Tyr Gln Ala Ser Ala Ala Ser Ile
                180                 185                 190

Ala Pro Gly Tyr Lys Pro Ser Thr Pro Val Pro Phe Leu Gly Glu Ala
            195                 200                 205

Glu His Gln Ala Thr Glu Glu Lys Gly Thr Glu Asn Lys Ala Asp Pro
210                 215                 220

Ser Asn Ser Pro Ser Ser Gly Ser His Ser Arg Ala Trp Glu Tyr Tyr
225                 230                 235                 240

Ser Arg Glu Lys Pro Lys Gln Glu Gly Glu Ala Lys Val Glu Ala His
                245                 250                 255

Arg Ala Gly Gln Gly His Pro Cys Arg Asn Ala Glu Ala Glu Glu Gly
                260                 265                 270

Gly Pro Glu Thr Thr Phe Val Cys Thr Gly Asn Ala Phe Leu Lys Ala
            275                 280                 285

Trp Val Tyr Arg Pro Gly Glu Asp Thr Glu Glu Glu Asp Asn Ser Asp
290                 295                 300

Ser Asp Ser Ala Glu Glu Asp Thr Ala Gln Thr Gly Ala Thr Pro His
305                 310                 315                 320

Thr Ser Ala Phe Leu Lys Ala Trp Val Tyr Arg Pro Gly Glu Asp Thr
                325                 330                 335

Glu Glu Glu Asp Ser Asp Ser Asp Ser Ala Glu Glu Asp Thr Ala Gln
                340                 345                 350

Thr Gly Ala Thr Pro His Thr Ser Ala Phe Leu Lys Ala Trp Val Tyr
            355                 360                 365

Arg Pro Gly Glu Asp Thr Glu Glu Asn Ser Asp Leu Asp Ser Ala
370                 375                 380
```

-continued

```
Glu Glu Asp Thr Ala Gln Thr Gly Ala Thr Pro His Thr Ser Ala Phe
385                 390                 395                 400

Leu Lys Ala Trp Val Tyr Arg Pro Gly Glu Asp Thr Glu Glu Glu Asn
            405                 410                 415

Ser Asp Leu Asp Ser Ala Glu Glu Asp Thr Ala Gln Thr Gly Ala Thr
            420                 425                 430

Pro His Thr Ser Pro Phe Leu Lys Ala Trp Val Tyr Arg Pro Gly Glu
            435                 440                 445

Asp Thr Glu Asp Thr Glu Glu Glu Asp Ser Glu Asn Val Ala
450                 455                 460

Pro Gly Asp Ser Glu Thr Ala Asp Ser Ser Gln Ser Pro Cys Leu Gln
465                 470                 475                 480

Pro Gln Arg Cys Leu Pro Gly Glu Lys Thr Lys Gly Arg Gly Glu Glu
            485                 490                 495

Pro Pro Leu Phe Gln Val Ala Phe Tyr Leu Pro Gly Glu Lys Pro Glu
            500                 505                 510

Ser Pro Trp Ala Ala Pro Lys Leu Pro Leu Arg Leu Gln Arg Arg Leu
            515                 520                 525

Arg Leu Phe Lys Ala Pro Thr Arg Asp Gln Asp Pro Glu Ile Pro Leu
            530                 535                 540

Lys Ala Arg Lys Val His Phe Ala Glu Lys Val Thr Val His Phe Leu
545                 550                 555                 560

Ala Val Trp Ala Gly Pro Ala Gln Ala Arg Gly Pro Trp Glu
            565                 570                 575

Gln Phe Ala Arg Asp Arg Ser Arg Phe Ala Arg Ile Ala Gln Ala
            580                 585                 590

Glu Glu Lys Leu Gly Pro Tyr Leu Thr Pro Asp Ser Arg Ala Arg Ala
            595                 600                 605

Trp Ala Arg Leu Arg Asn Pro Ser Leu Pro Gln Ser Glu Pro Arg Ser
            610                 615                 620

Ser Ser Glu Ala Thr Pro Leu Thr Gln Asp Val Thr Thr Pro Ser Pro
625                 630                 635                 640

Leu Pro Ser Glu Thr Pro Ser Pro Ser Leu Tyr Leu Gly Gly Arg Arg
            645                 650                 655

Gly
```

(2) INFORMATION FOR SEQ ID NO:4:

(i) SEQUENCE CHARACTERISTICS:
        (A) LENGTH: 590 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 452490

(xi) SEQUENCE DESCRIPTION: SEQ ID NO:4:

```
Met Ala Pro Ser Pro Arg Pro Gln His Ile Leu Leu Trp Arg Asp Ala
1               5                   10                  15

His Ser Phe His Leu Leu Ser Pro Leu Met Gly Phe Leu Ser Arg Ala
            20                  25                  30

Trp Ser Arg Leu Arg Val Pro Glu Ala Pro Glu Pro Trp Pro Ala Glu
            35                  40                  45

Thr Val Thr Gly Ala Asp Gln Ile Glu Ala Asp Ala His Pro Ala Pro
```

-continued

```
                50                  55                  60
Pro Leu Val Pro Glu Asn His Pro Gln Gly Glu Ala Glu Ser
65                  70                  75                  80
Gly Thr Pro Glu Glu Gly Lys Ala Ala Gln Gly Pro Cys Leu Asp Val
                85                  90                  95
Gln Ala Asn Ser Ser Pro Pro Glu Thr Leu Gly Leu Ser Asp Asp Asp
                100                 105                 110
Lys Gln Gly Gln Asp Gly Pro Arg Glu Gln Gly Arg Ala His Thr Ala
                115                 120                 125
Gly Leu Pro Ile Leu Leu Ser Pro Gly Leu Gln Ser Ala Asp Lys Ser
                130                 135                 140
Leu Gly Glu Val Val Ala Gly Glu Gly Val Thr Glu Leu Ala Tyr
145                 150                 155                 160
Pro Thr Ser His Trp Glu Gly Cys Pro Ser Glu Glu Glu Asp Gly
                165                 170                 175
Glu Thr Val Lys Lys Ala Phe Arg Ala Ser Ala Asp Ser Pro Gly His
                180                 185                 190
Lys Ser Ser Thr Ser Val Tyr Cys Pro Gly Glu Ala Glu His Gln Ala
                195                 200                 205
Thr Glu Glu Lys Gln Thr Glu Asn Lys Ala Asp Pro Pro Ser Ser Pro
                210                 215                 220
Ser Gly Ser His Ser Arg Ala Trp Glu Tyr Cys Ser Lys Gln Glu Gly
225                 230                 235                 240
Glu Ala Asp Pro Glu Pro His Arg Ala Gly Lys Tyr Gln Leu Cys Gln
                245                 250                 255
Asn Ala Glu Ala Glu Glu Glu Glu Ala Lys Val Ser Ser Leu Ser
                260                 265                 270
Val Ser Ser Gly Asn Ala Phe Leu Lys Ala Trp Val Tyr Arg Pro Gly
                275                 280                 285
Glu Asp Thr Glu Asp Asp Asp Ser Asp Trp Gly Ser Ala Glu Glu
                290                 295                 300
Glu Gly Lys Ala Leu Ser Ser Pro Thr Ser Pro Glu His Asp Phe Leu
305                 310                 315                 320
Lys Ala Trp Val Tyr Arg Pro Gly Glu Asp Thr Glu Asp Asp Asp
                325                 330                 335
Ser Asp Trp Gly Ser Ala Glu Glu Gly Lys Ala Leu Ser Ser Pro
                340                 345                 350
Thr Ser Pro Glu His Asp Phe Leu Lys Ala Trp Val Tyr Arg Pro Gly
                355                 360                 365
Glu Asp Thr Glu Asp Asp Gln Asp Ser Asp Trp Gly Ser Ala Glu Lys
                370                 375                 380
Asp Gly Leu Ala Gln Thr Phe Ala Thr Pro His Thr Ser Ala Phe Leu
385                 390                 395                 400
Lys Thr Trp Val Cys Cys Pro Gly Glu Asp Thr Glu Asp Asp Cys
                405                 410                 415
Glu Val Val Pro Glu Asp Ser Glu Ala Ala Asp Pro Asp Lys Ser
                420                 425                 430
Pro Ser His Glu Ala Gln Gly Cys Leu Pro Gly Glu Gln Thr Glu Gly
                435                 440                 445
Leu Val Glu Ala Glu His Ser Leu Phe Gln Val Ala Phe Tyr Leu Pro
                450                 455                 460
Gly Glu Lys Pro Ala Pro Pro Trp Thr Ala Pro Lys Leu Pro Leu Arg
465                 470                 475                 480
```

-continued

```
Leu Gln Arg Arg Leu Thr Leu Leu Arg Thr Pro Thr Gln Asp Gln Asp
                485                 490                 495

Pro Glu Thr Pro Leu Arg Ala Arg Lys Val His Phe Ser Glu Asn Val
            500                 505                 510

Thr Val His Phe Leu Ala Val Trp Ala Gly Pro Ala Gln Ala Ala Arg
        515                 520                 525

Arg Gly Pro Trp Glu Gln Leu Ala Arg Asp Arg Ser Arg Phe Ala Arg
    530                 535                 540

Arg Ile Ala Gln Ala Glu Glu Lys Leu Gly Pro Tyr Leu Thr Pro Ala
545                 550                 555                 560

Phe Arg Ala Arg Ala Trp Ala Arg Leu Gly Asn Pro Ser Leu Pro Leu
            565                 570                 575

Ala Leu Glu Pro Ile Cys Asp His Thr Phe Phe Pro Ser Gln
            580                 585                 590
```